(12) United States Patent
Dalton

(10) Patent No.: US 7,374,534 B2
(45) Date of Patent: May 20, 2008

(54) RETRACTOR AND METHOD FOR PERCUTANEOUS TISSUE RETRACTION AND SURGERY

(76) Inventor: Brian E. Dalton, 333 State St., Erie, PA (US) 16507

( * ) Notice: Subject to any disclaimer, the term of this patent is extended or adjusted under 35 U.S.C. 154(b) by 518 days.

(21) Appl. No.: 11/077,329

(22) Filed: Mar. 9, 2005

(65) Prior Publication Data
US 2006/0206008 A1   Sep. 14, 2006

(51) Int. Cl.
*A61B 1/32* (2006.01)

(52) U.S. Cl. .................. 600/222; 600/224

(58) Field of Classification Search ........... 600/214, 600/215, 219, 220, 222, 224
See application file for complete search history.

(56) References Cited

U.S. PATENT DOCUMENTS

| | | | | |
|---|---|---|---|---|
| 52,014 A | * | 1/1866 | Bartlett | ............ 600/224 |
| 58,709 A | * | 10/1866 | Worrall | ............ 600/213 |
| 380,745 A | * | 4/1888 | Chamberlin | ............ 600/224 |
| 5,667,520 A | | 9/1997 | Bonutti | |
| 5,685,826 A | | 11/1997 | Bonutti | |
| 5,716,325 A | * | 2/1998 | Bonutti | ............ 600/204 |
| 5,888,196 A | | 3/1999 | Bonutti | |
| 6,478,028 B1 | * | 11/2002 | Paolitto et al. | ............ 128/898 |
| 6,837,891 B2 | | 1/2005 | Davison et al. | |
| 2003/0191371 A1 | | 10/2003 | Smith et al. | |
| 2005/0137461 A1 | * | 6/2005 | Marchek et al. | ............ 600/220 |
| 2006/0142643 A1 | * | 6/2006 | Parker | ............ 600/219 |

* cited by examiner

*Primary Examiner*—Cary E O'Connor
(74) *Attorney, Agent, or Firm*—Carothers & Carothers

(57) ABSTRACT

A retractor for percutaneous surgery in a patient which includes an elongate retractor tube composed of circumferentially arranged elongate independent tube segments with proximal ends of the tube segments respectively hinged to a unitary collar whereby the distal ends of the tube segments may be outwardly expanded in umbrella fashion by outwardly pivoting the segments about their respective hinges for thereby retracting surrounding tissue. The distal end of the retractor tube is provided with a tapered distal end suitably dimensioned for insertion into a stab incision. An internally open expansion collet is coaxially received in the collar for adjustable coaxial advancement downwardly into the collar toward the retractor tube segments and fulcrum tabs protrude inwardly and upwardly towards the expansion collet from each tube segment adjacent a respective hinge. The fulcrum tabs are sized for engaging a bottom end of the collet for thereby progressively pivoting the segments outward about their hinges as the collet advances downwardly into the collar.

15 Claims, 6 Drawing Sheets

RETRACTOR AND METHOD FOR PERCUTANEOUS TISSUE RETRACTION AND SURGERY

BACKGROUND OF THE INVENTION

The present invention relates to expandable retractors for use in surgery. More particularly, the present invention relates to mechanical selectively expandable retractors for moving subsurface tissue in surgery performed percutaneously through a stab incision for performing minimally invasive surgical techniques.

Traditional open surgical procedures performed on locations deep within the body can cause significant trauma to the intervening tissues. Such procedures often require along incision, extensive muscle stripping, prolonged retraction of tissues, denervation and devascularication of tissue. These traditional open surgeries can require extensive operating time and extensive post-operative recovery time, and in some cases, can lead to permanent scarring and more severe pain to the patient.

Accordingly minimally invasive surgical procedures are preferred. Such minimal access procedures utilize a device to expose the operative field with a minimum of trauma to surrounding tissues, most notably musculature. These minimal access devices or retractors generally rely on splitting muscle planes to reach desired operative fields. Accordingly, this minimally invasive approach is more desirable than standard surgical operations which rely on stripping musculature off its attachments. It is an object of the present invention to provide a retractor for minimally invasive surgery which eliminates the requirement of multiple steps to dilate the musculature, or most notably eliminates the requirement or use of a "tube over tube" sequential dilation system, as well as the elimination of the adaptation and use of standard retractor systems for minimal access surgery.

SUMMARY OF THE INVENTION

The retractor of the present invention provides a one step expandable access device which is employed percutaneously through a single stab incision with or without the use of guiding K-Wire. In addition, the retractor of the present invention can be preset so that the minimal access device expands either asymmetrically or differentially (non-asymmetrically) to allow maximization of use of the operative field depending upon the anatomical restrictions of the operative field, thereby providing a retractor which is adaptable to a variety of surgical conditions.

The retractor of the present invention is suitable for percutaneous surgery applied through a small stab incision and the retractor is comprised of an elongate retractor tube having top and bottom ends and which is composed of circumferentially arranged elongate independent tube segments which are separable from each other and have distal and proximal ends with their proximal top ends respectively hinged to a unitary collar. Accordingly, the distal ends of the tube segments may be outwardly expanded by outwardly pivoting these tube segments about their respective proximal hinges for thereby retracting surrounding tissue. It is preferable that the distal ends of the retractor tube segments either collectively, or with the inclusion of a removable obturator tip, form a tapered distal end which is suitably dimensioned for insertion into a stab incision.

The tube segments may be mechanically expanded outward at their distal ends through the use of a mechanism which includes an internally open expansion collet that is coaxially received in the aforesaid collar for adjustable coaxially advancement downwardly into this collar towards the retractor body. Fulcrum tabs protrude inwardly and upwardly toward the collet from each tube segment adjacent a respective of the hinges and these fulcrum tabs are sized for engaging a bottom end of the expansion collet for thereby progressively pivoting the segments outward about their respective hinges as the collet advances downwardly into the collar for thereby retracting surrounding tissue. This expansion collet is preferably threadably received within the collar for threaded advancement or retraction in the collar.

The fulcrum tabs may be provided in different or varying sizes and dimensions for thereby correspondingly varying the extent of expansion of the tube segments, whereby the distal end of one tube segment may be expanded outwardly more or less than those of the distal ends of the remaining tube segments. This permits differentially or non-asymmetrical expansion of the retractor.

Another embodiment of the retractor of the present invention further provides these tube segments with the capability of being extendable also in their longitudinal direction for thereby extending their overall length. In this embodiment, an extension collet is coaxially received in the aforesaid expansion collet for thereby engaging and slidably extending lower portions of the tube segments longitudinally. This extension collet may be threadably received in the expansion collet for threadable advancement or retraction therein. The lower portions of the tube segments are slidably received in respective upper portions of the tube segments in keyed relationship whereby they maintain their longitudinal alignment while being extended or retracted.

Optionally an obturator tip may be provided in any of the embodiments of the retractor of the present invention whereby the tip protrudes from the lower distal ends of the tube segments. This obturator tip is connected to the extension collet, in the extendable version of the tube segments, or to an obturator head, in the non-longitudinally extendable version of the retractor of the present invention, via a stem for thereby providing in combination an obturator. The obturator is removable upon expansion of the tube segments so that the surgeon has clear access to the surgical site through the retractor of the present invention.

In addition, the obturator may be cannulated to permit the passage and use of a guiding K-wire.

In the longitudinally extendable embodiment of the retractor of the present invention, the obturator tip is engaged with the lower portions of the tube segments when they are collapsed for extending these tube segments longitudinally therewith when the obturator head is screwed downwardly into the expansion collet.

An attachment arm extends laterally from the expansion collet for externally supporting the retractor during the surgical procedure, which allows the retractor to be attached to a separate flexible Leyla-type retractor arm for securing the device during operation.

The retractor body in its collapsed state may take on various configurations, such as cylindrical with a tapered distal tip or end, a continuously inwardly tapered form from the collar to the tip, or the tube segments may take on an outwardly bowed or bulbous configuration in their collapsed condition which allows for an umbrella type expansion and exposure of the operative field.

BRIEF DESCRIPTION OF THE DRAWINGS

Other objects and advantages appear hereinafter in the following description and claims. The accompanying drawings show, for the purpose of exemplification, without limiting the scope of the invention or appended claims, certain practical embodiments of the present invention wherein:

DETAILED DESCRIPTION OF THE PREFERRED EMBODIMENTS

Figure 5:
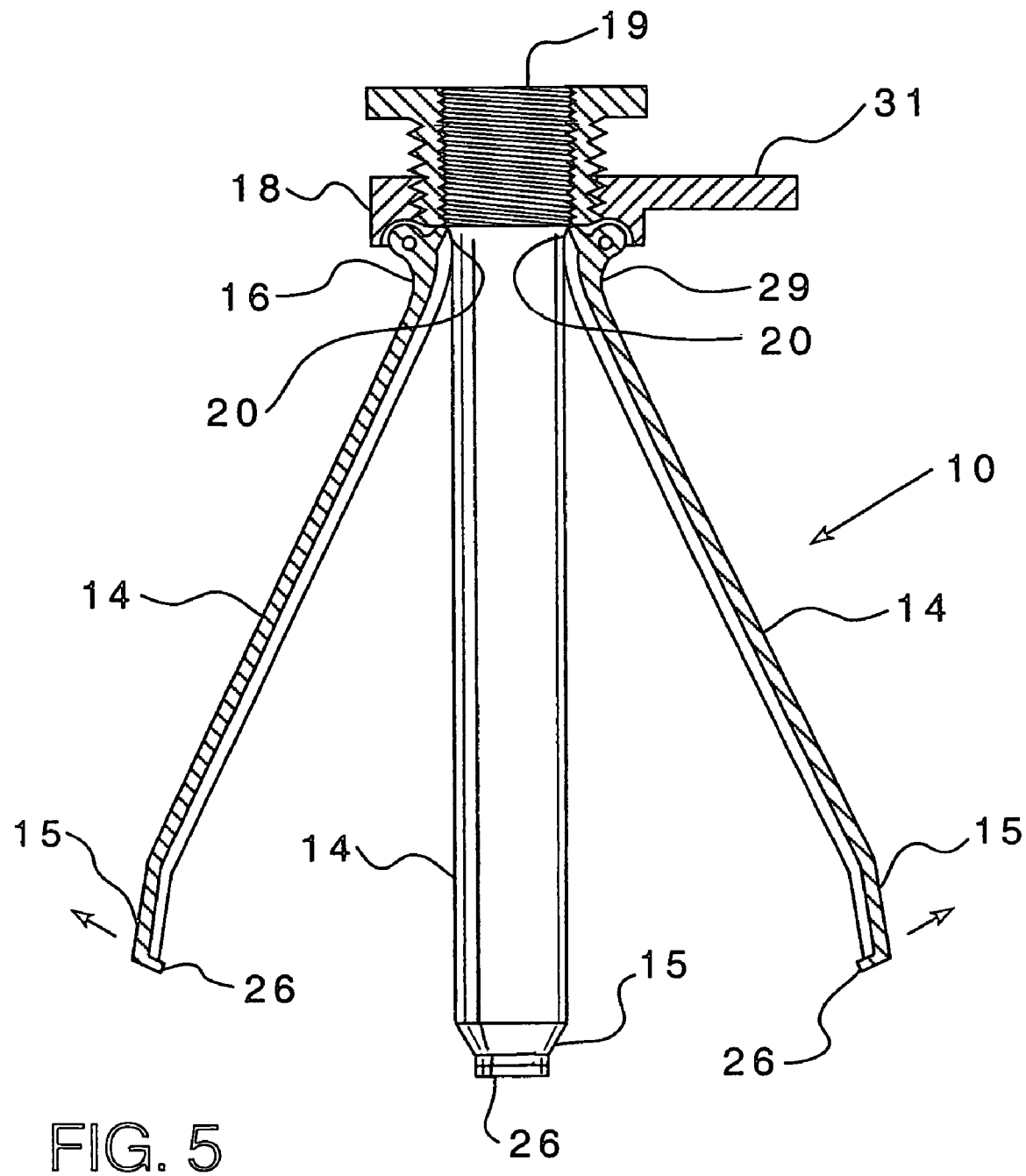
FIG. 5 is a view in vertical mid cross section of the retractor shown in FIG. 1 in an expanded condition with the central obturator removed.

Referring to FIGS. 1 through 4, the retractor 10 of the present invention is comprised of a composite elongate retractor tube 11 having top and bottom ends 12 and 13 and composed of four circumferentially arranged elongate independent tube segments 14 having distal and proximal ends 15 and 16 respectively with the proximal ends 16 respectively hinged at 17 to unitary collar 18. Accordingly, the distal ends 15 may be outwardly expanded by outwardly pivoting the segments 14 about the respective hinges 17 for thereby retracting surrounding tissue as illustrated in FIG. 5.

The mechanism for actuating the expansion of tube segments 14 includes an internally open expansion collet 19 coaxially received in collar 18 for adjustable coaxial advancement downwardly into collar 18 by threaded engagement toward the retractor tube segments 14.

Fulcrum tabs 20 protrude inwardly and upwardly toward collet 19 from each tube segment 14 adjacent a respective of the hinges 17. These fulcrum tabs are sized or dimensioned for engaging a bottom end 21 of collet 19 for thereby progressively pivoting the segments 14 about their respective hinges 17 as collet 19 advances downwardly into collar 18. The Fulcrum tabs may be varied in size or length for correspondingly varying the extent of expansion of segments 14. It can be seen that use of a shorter fulcrum tab 20 will cause the respective tube segment 14 to pivot outwardly as shown in FIG. 5 to a lesser degree, whereas the use of a longer fulcrum tab 20 will cause the respective tube segment 14 to be pivoted outwardly to a larger degree than that shown in FIG. 5. Accordingly, by so adjusting the size of the fulcrum tabs, the retractor 10 of the present invention may be expanded asymmetrically or non-asymmetrically to allow maximization of use of the operative field depending upon the anatomical restrictions of the field.

A central obturator 22 is provided and consists of an obturator head 23 threadably received in expansion collet 19, an obturator tip 24 protruding from the distal lower ends 15 of tube segments 14 and a stem 25 connecting obturator head 23 to obturator tip 24. Once tube segments 14 have been expanded as illustrated in FIG. 5, obturator 22 may then be removed by treadably disengaging obturator head 23 from expansion collet 19 and then removing the entire obturator 22 from the field thereby leaving access to the operating site through the hollow interior of expansion collet 19 and expanded tube segments 14.

Figures 1, 2:
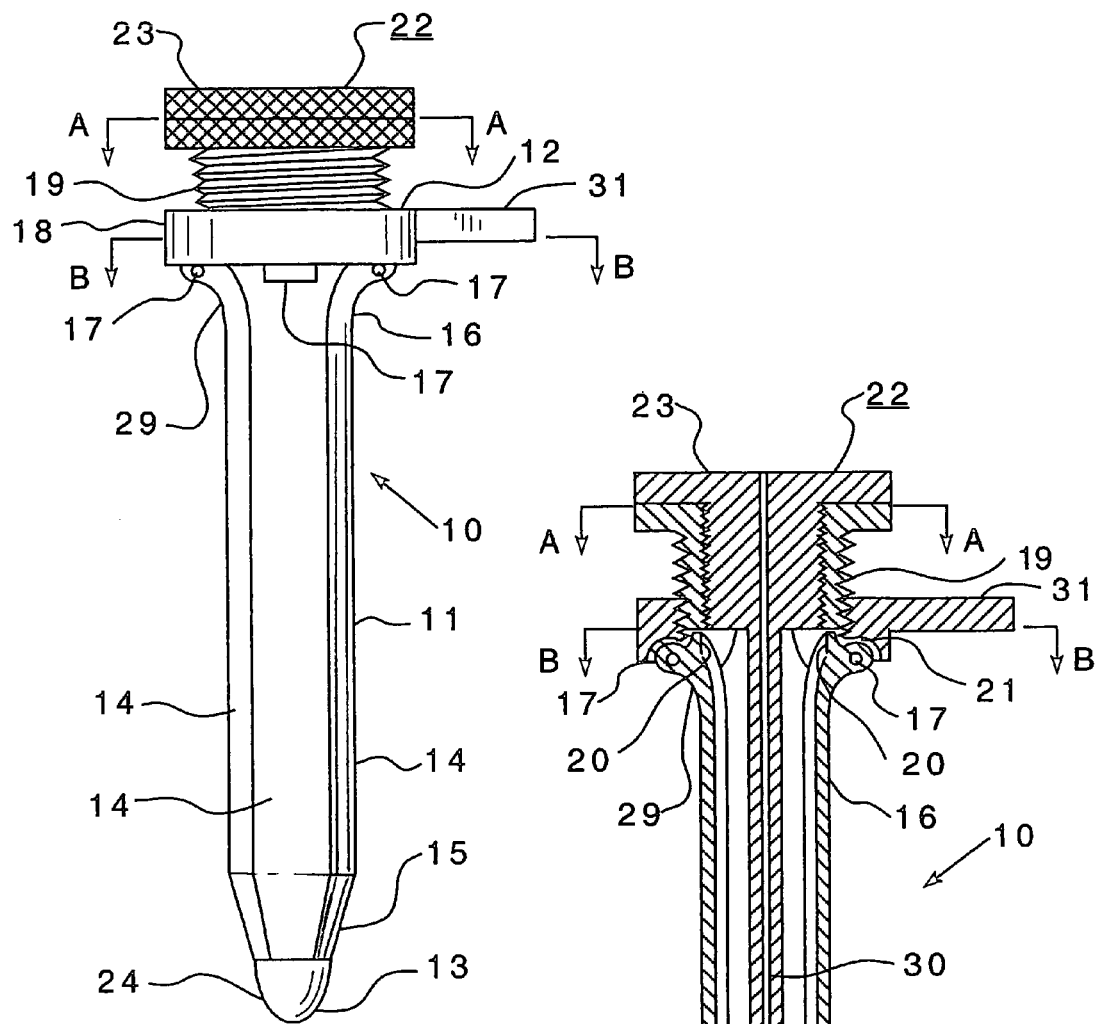
FIG. 1 is a view in front elevation of one embodiment of the retractor of the present invention.
FIG. 2 is a view in vertical mid cross section of the retractor shown in FIG. 1.
Figure 3:
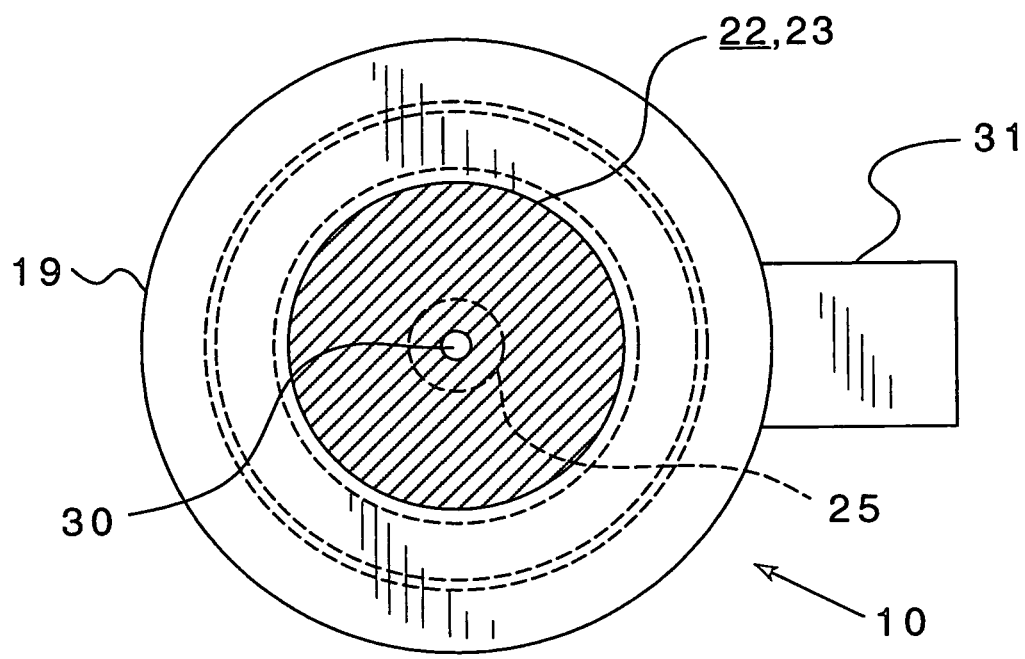
FIG. 3 is an enlarged view in cross section of the retractor shown in FIG. 1 as seen along section line A-A.
Figure 4:
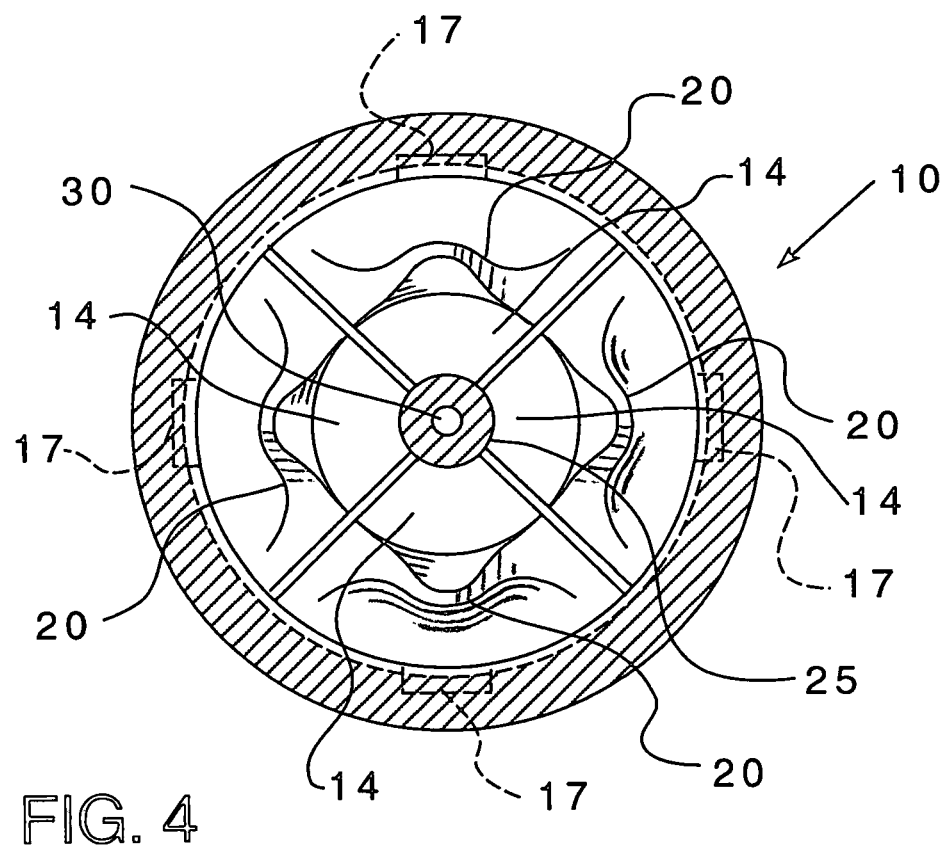
FIG. 4 is an enlarged view in cross section of the retractor shown in FIG. 1 as seen along section B-B.

It should be noted particularly in FIG. 2 that the distal ends 15 of tube segments 14 have in-turned protrusions 26 which are correspondingly received in an annular groove 27 at the bottom of stem 25 adjacent the obturator tip 24. In this configuration, obturator head 23 may be slightly unscrewed or withdrawn from expansion collet 19 whereby the upper annular face 28 of obturator head 24 slightly presses upwardly against protrusions 26 thereby maintaining them in position and preventing them from expanding while the obturator tip 24 is being inserted into a stab incision. Once the retractor 10 is in position, having been inserted into a stab incision provided in the patient to a level indicated at 29, pressure applied by the upper end 28 of obturator head 24 against inwardly directed protrusions 26 may be relieved and the tubular segments 14 expanded as previously described by downwardly screwing expansion collet 19 into collar 18 as illustrated in FIG. 5. Then obturator 22 is removed by threadably disengaging obturator head 23 from expansion collet 19.

Obturator 22 is cannulated as shown by the central passage 30 which allows the use of a guiding K-wire. The collar 18 is also provided with a rigid attachment arm 31 extending laterally therefrom for externally supporting the retractors such as with the use of a separate flexible Leyla-type retractor arm (not shown) for securing the device during operation.

Figure 6:
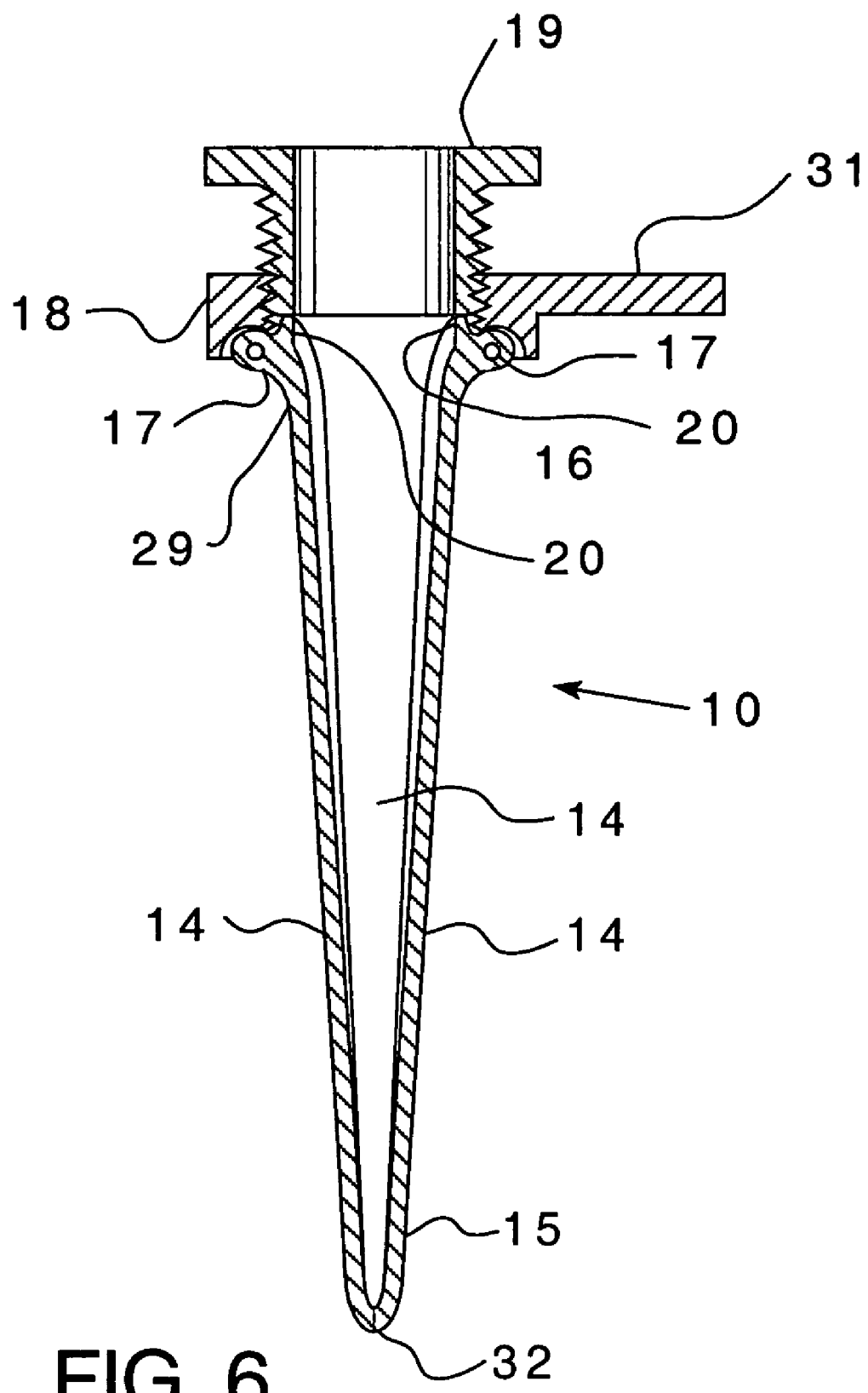
FIG. 6 is a view in vertical mid cross section illustrating a variation in the embodiment of the retractor shown in FIG. 1 which eliminates the requirement of a central obturator and illustrates a variation in the outside configuration of the retractor body.
Figure 7:
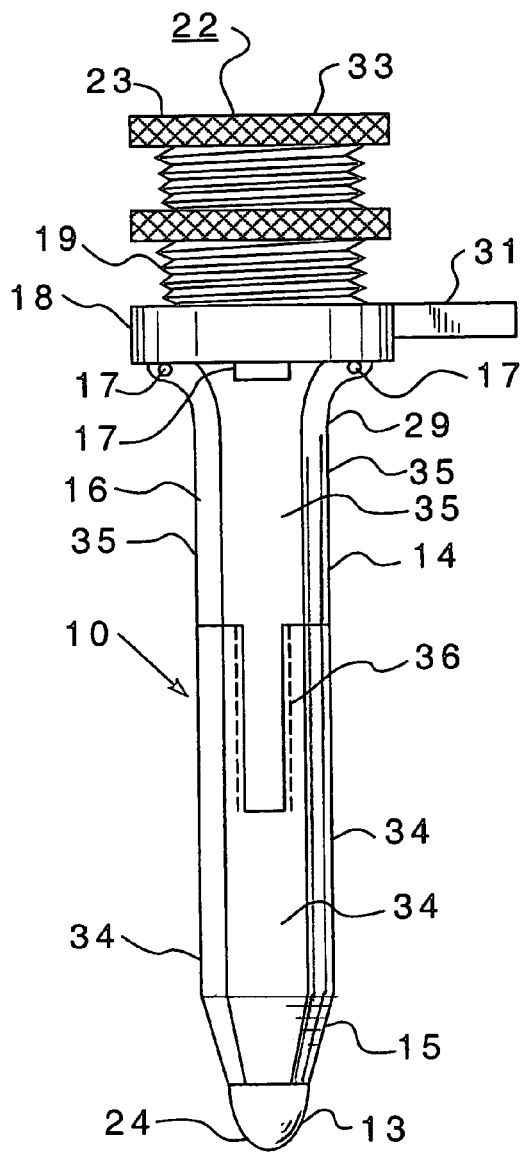
FIG. 7 is a view in front elevation of another embodiment of the retractor of the present invention which incorporates longitudinally extendable tube segments.
Figure 8:
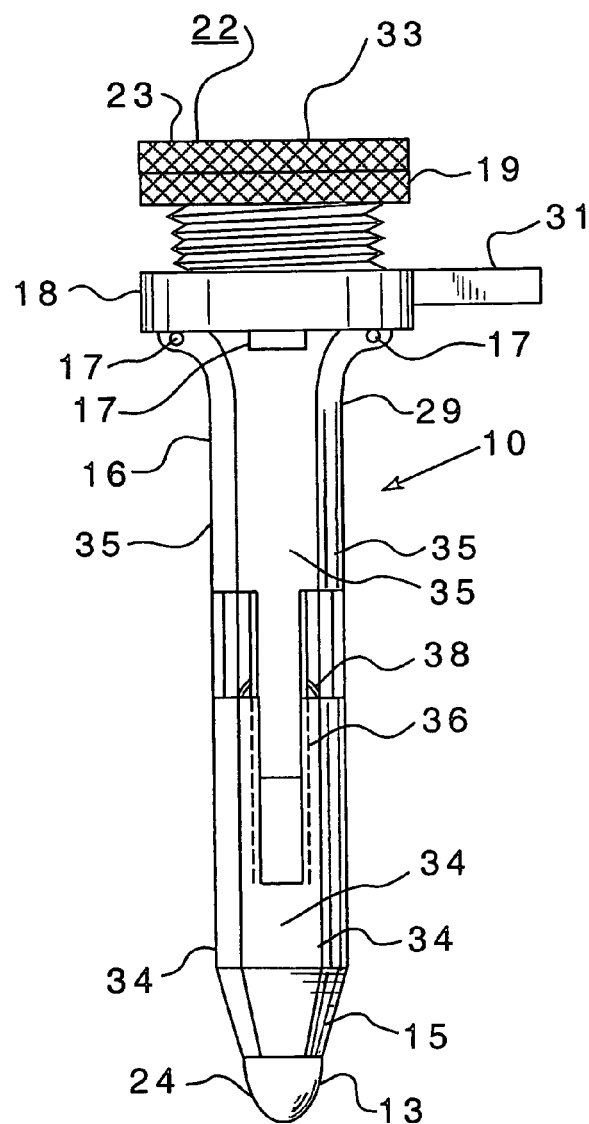
FIG. 8 illustrates the retractor shown in FIG. 7 with the tube elements extended.

FIG. 6 illustrates a variation or another embodiment of the retractor 10 wherein the incorporation of an obturator 22 as shown in the previous figures is completely eliminated. In this embodiment the tube segments 14 in their collapsed configuration as shown in FIG. 6 are tapered inwardly from their proximal ends 16 to their distal ends 15 and in this collapsed condition they form at their distal end 15 a suitable tapered distal end 32 for percutaneous insertion into a stab incision. In this embodiment, again four tube segments 14 are illustrated, however it is possible to construct the retractor 10 of only two tube segments but it is preferable to use three or more tube segments 14 in order to provide adequate circumferential expansion of the surrounding subsurface tissue. Also in this embodiment the tube segments 14 in their collapse condition is illustrated in the figure having a tapered configuration as opposed to the cylindrical configuration shown in the previous figures. Also, other shapes are possible such as a bulbous shape which can provide an umbrella expansion effect when the tube segments 14 are expanded.

Referring next to the embodiment illustrated in FIGS. 7 through 10, this embodiment of retractor 10 provides tube segments 14 which are extendable in their longitudinal direction for thereby extending their overall length of the retractor 10. In this embodiment an extension collet 33 is threadably and coaxially received in expansion collet 19. In this particular embodiment, extension collet 33 is in fact the same as obturator head 23 of obturator 22. When extension collet 33 is threadably advanced downwardly into expansion collet 19 it engages and pulls the lower portions 34 of tube segments 14 downwardly or longitudinally. This is accomplished because the obturator 22 pulls the lower portion 34 downwardly by reason of the engagement of tube segment protrusions 26 into annular groove 27 of obturator stem 25. Once the desired length of downward extension of tube segments 14 has been obtained, then the retractor 10 may be expanded as previously described by screwing expansion collet 19 downwardly into collar 18.

The lower portions 34 of segments 14 are slidably received in respective upper portions 35 in keyed relationship as illustrated by the tongue and groove slide 36. This maintains the upper portions 35 and the lower portions 34 in longitudinal alignment as the two portion are being extended relative to each other. The lower portions 34 of segments 14 are also maintained in position relative to upper portions 34 as the lower portions 34 are being extended downwardly or longitudinally by means of a ratchet mechanism.

Figure 9:
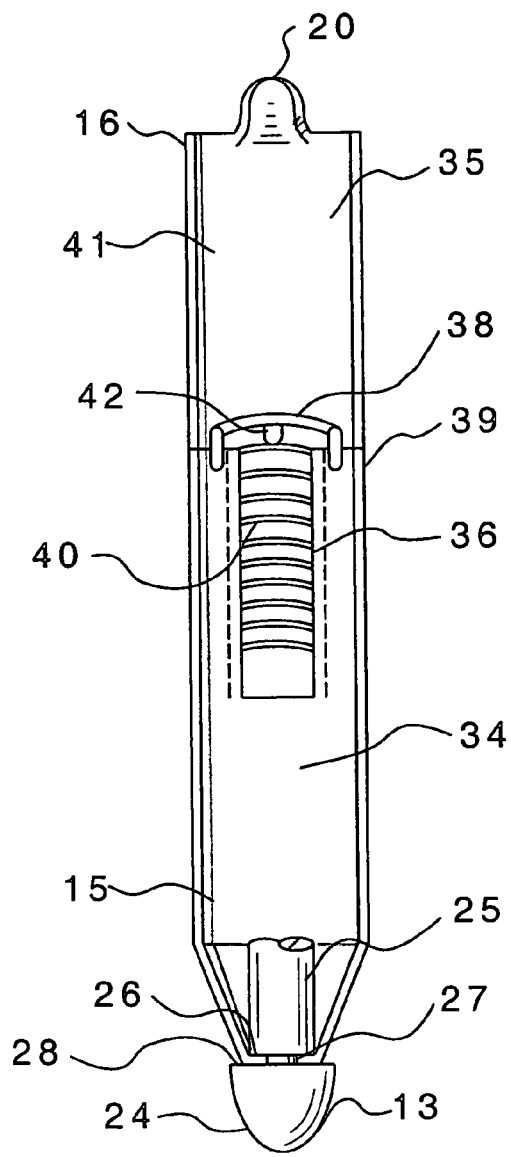
FIG. 9 is a view in front elevation showing the inside of one of the extendable tube segments of the retractor shown in FIG. 7.
Figure 10:
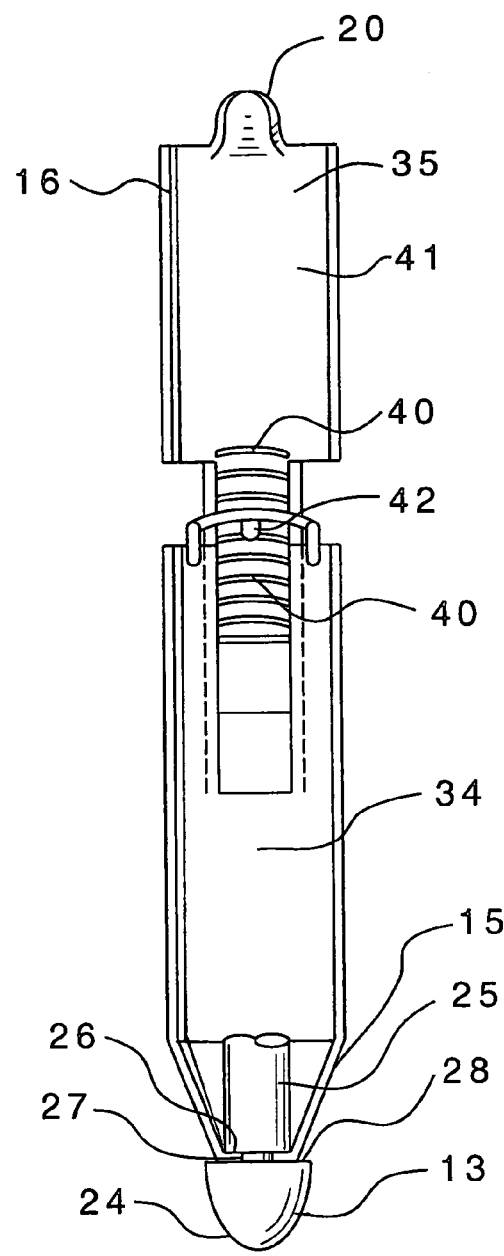
FIG. 10 illustrates the retractor tube segment of FIG. 9 shown in a longitudinally extended condition.

This ratchet mechanism is best illustrated in FIGS. 9 and 10 and is comprised of a flexible spring wire 38 which is secured at opposite ends into the upper end 39 of lower portion 36 in combination with the elliptical segment grooves 40 serially provided within the inner surface 41 of upper portion 35. As the lower portions 34 are being forced downwardly away from upper portions 35, the ratchet spring wire 38 is so dimensioned and formed whereby it protrudes into and ratchets downwardly from one slot 40 to the next descending slot 40 to thereby retain the lower portion 35 in position at its newly extended location relative to upper portion 35.

If it is desired to retract lower portions 34 after being extended, this may be done so by engaging tabs 42 through the open interior of retractor 10 with a hook shaped instrument (not shown). Tabs 42 are welded securely to ratchet spring wires 38 and thus by pulling upward on tab 42 with the appropriate instrument the spring wire 38 is released from its respective groove 40 in which it is lodged so that the entire lower portion 34 may be slid upwardly toward its upper portion 35.

The operative technique will now be described using K-wire. In this instance, K-wire will be utilized to guide the retractor 10 as well as to mark the operative site. Using fluoroscopy, the appropriate level is visualized and then a small stab incision is planned to allow approach to the operative site. Then the stab incision is made and the K-wire is advanced through the stab incision down to the operative site, which in this instance is designated to be in the area of the spine.

The fascia overlying the spine in this area is then incised to allow ease of insertion and the K-wire is then inspected for the appropriate depth of the retraction, the K-wire being marked with centimeter markings. The appropriate retractor 10 of the present invention with that range of depth would be chosen, or the extendable version of the retractor 10 of the present invention would be employed and slipped over the K-wire and then advanced down to the hinge line to level 29 as illustrated in FIG. 1 along the K-wire. Once the retractor 10 is in position, the obturator 22 would be compressed or pushed to drive the obturator tip 24 towards the operative site. Once the obturator tip 24 comes in contact with the operative site, then the retractor 10 is expanded as previously explained by downwardly advancing the expansion collet 19 into collar 18 thereby expanding the retractor tube segments 14 to the desired extent. Once this has occurred, because of the shape of the tapered retractor body, the retractor should actually advance into the wound once the tapered portion of the retracted body is in pressure fit with the surrounding fascia.

The attachment arm 31 is then attached to an appropriate support such as a flexible Leyla-type retractor arm for securing the retractor 10. Then the obturator 22 would be removed from the central portion of the retractor 10 by unscrewing the obturator head 23 from expansion collet 19. Obturator 22 would be removed along with the K-wire. This now allows full visualization of the operative field and the expansion collet 19 may be further turned downwardly into collar 18 to allow further visualization of the operative field as desired by the surgeon. The advancement is continued until the surgeon is satisfied with the exposure. Once this is completed, the Leyla-arm holding the attachment arm 31 would be tightened to its final position and the operation can then proceed.

In summary, the retractor 10 of the present invention provides a one step device meaning that multiple pieces are not required that need to be assembled in application nor is there required the conventional "tube over tube" type system of other retractors. The retractor device 10 of the present invention also accounts for varying depths of the wound without the need for one device for every half centimeter or centimeter of wound depth. This is owing to the fact that the retractor segments 14 are expandable and/or extendable. Also, the retractor 10 of the present invention further provides for differential expansion of the segments 14 to accommodate a variety of anatomical conditions.

The retractor 10 of the present invention can be used with or without a guiding K-wire as desired and may be used without an obturator 22. In either event, either the obturator tip 24 or the tube segment tip 32 in the embodiment of FIG. 6 provides a smooth passage of the device. Also, because the retractor tube segments 14 articulate with the tip 24 of the obturator 22, this guards against the premature expansion of the segments 14 during the insertion of the device.

I claim:

1. A retractor for percutaneous surgery in a patient comprising:
    an elongate retractor tube having top and bottom ends and comprised of circumferentially arranged elongate independent tube segments having distal and proximal ends with said proximal ends respectively hinged to a unitary collar whereby said distal ends may be outwardly expanded by outwardly pivoting said segments about their respective hinges for thereby retracting surrounding tissue;
    said segments being extendable in their longitudinal direction for thereby extending their overall length; and
    including an extension collet coaxially received in said collar for thereby engaging and slidably extending lower portions of said segments longitudinally.

2. The retractor of claim 1, wherein the distal ends of said retractor tube segments collectively form a tapered distal end when collapsed together which is suitably dimensioned for insertion into a stab incision.

3. The retractor of claim 1, including an internally open expansion collet coaxially received in said collar for adjustable coaxial advancement downwardly into said collar toward said retractor tube segments; and
    fulcrum tabs protruding inwardly and upwardly toward said expansion collet from each tube segment adjacent a respective of said hinges, and sized for engaging a bottom end of said expansion collet for thereby progressively pivoting said segments outward about said hinges as said expansion collet advances downwardly into said collar.

4. The retractor of claim 3, wherein said retractor has a tapered distal bottom end providing a tip suitably dimensioned for insertion into a stab incision.

5. The surgical retractor of claim 3, wherein said expansion collet is threadably received in said collar.

6. The surgical retractor of claim 3, wherein said fulcrum tabs vary in size for corresponding varying the extent of expansion of said segments.

7. The surgical retractor of claim 1, wherein said extension collet is threadably received in said collar.

8. The surgical retractor of claim 1, wherein said lower portions of said segments are slidably received in respective upper portions thereof in keyed relationship.

9. The surgical retractor of claim 1, including an obturator tip protruding from the distal lower ends of said segments, said tip connected to said extension collet via a stem for thereby providing in combination an obturator, said obturator being removable upon expansion of said segments.

10. The surgical retractor of claim 9, wherein said obturator is cannulated.

11. The surgical retractor of claim 9, wherein said obturator tip is engaged with said lower portion of segments when collapsed for extending said segments longitudinally therewith.

12. The surgical retractor of claim 1, including ratchet means for retaining said lower portions of said segments in temporary fixed relationship to said upper portions.

13. The surgical retractor of claim 1, including an attachment arm extending laterally from said collar for externally supporting said retractor.

14. The surgical retractor of claim 1, including at least three of said segments.

15. The surgical retractor of claim 1, wherein said retractor body is inwardly tapered from said collar to said tip.

* * * * *